US006162473A

United States Patent [19]
Fodge et al.

[11] Patent Number: 6,162,473
[45] Date of Patent: Dec. 19, 2000

[54] HEMICELLULASE USE IN FEEDS WITH LOW CALORIC CONTENT

[75] Inventors: Douglas W. Fodge; Humg-Yu Hsiao, both of Rockville, Md.

[73] Assignee: Chemgen Corporation, Gaithersburg, Md.

[21] Appl. No.: 09/180,105

[22] PCT Filed: May 2, 1997

[86] PCT No.: PCT/US97/05406

§ 371 Date: Dec. 3, 1998

§ 102(e) Date: Dec. 3, 1998

[87] PCT Pub. No.: WO97/41739

PCT Pub. Date: Nov. 13, 1997

Related U.S. Application Data
[60] Provisional application No. 60/038,954, May 3, 1996.

[51] Int. Cl.$^7$ ................................ A23K 1/00; A23L 1/20
[52] U.S. Cl. ................................ 426/53; 426/46; 426/630
[58] Field of Search .................................. 426/53, 54, 46, 426/630, 807

[56] References Cited

U.S. PATENT DOCUMENTS

| | | | |
|---|---|---|---|
| 3,365,440 | 1/1968 | Circle et al. | 260/123.5 |
| 4,822,814 | 4/1989 | Ohyama et al. | 514/440 |
| 5,429,828 | 7/1995 | Fodge et al. | 426/18 |
| 5,476,775 | 12/1995 | Fodge et al. | 435/209 |
| 5,723,443 | 3/1998 | Kagawa et al. | 514/18 |

OTHER PUBLICATIONS

Easter et al., Dietary nututrient allowances for swine, Adjustments to nutrient allowance, Feedstuffs, (Jul. 1995), pp 41, 44 and 46.
Park W. Walthrop, Dietary nutrients allowances for poultry, Feedstuffs, (Jul. 1995), pp 69–72, 74 and 76.
Nick Dale, Ingredient analysis table: 1995 edition, Feedstuffs, (Jul. 1995), pp 24, 31, 32, 34, 36, 38, 39.
Schwartz et al., Journal of Agricultural and Food Chemistry, A Publication of the American Chemical Society, vol. 10, No. 2 (1962), pp 131–133.
R. L. Whistler, Polysaccharide Chemistry, Academic Press, Inc., (1953), pp 292–303.
R. T. Rowlands, Review: Industrial strain improvement: mutagenesis and random screening procedures, Enzyme Microb. Technology, vol. 6, (1984), pp 3–10.
Hansson et al., "The Journal of Biological Chemistry", Expression and Characterization of Biologically Active Human Extracellular Superoxide Dismutase in Milk of Transgenic Mice, vol, 269, No. 7, (1994).
Velander et al., Proceedings of the National Academy of Sciences:, High–level expression of a heterologous protein in the milk of transgenic swine using the cDNA encoding human protein C transgenic swine using the cDNA encoding human protein C, (1992), pp 12003–12007.
Whistler et al., Polysaccharide Chemistry, Academic Press, Inc., (1953), pp 152–161.

Biely et al., [65] Remazole Brilliant Blue–Xylan: A Soluble Chromogenic Substrate for Xylanases, Methods in Enzymology, vol. 160, (1967), pp 536–541.
Van Rooijen et al., Plant Seed Oil–Bodies as Carriers for Foreign Proteins, Bio/Technology, vol. 13, (1995), pp 72–77.
Emi et al., Crystallization and Some Properties of Mannanase, [Agr. Biol. Chem., vol. 36, No. 6, (1972), pp 991–1001.
Kusakabe et al., β–Mannanase of Streptomyces, Methods in Enzymology vol. 160, pp 611–615 (date N.A.).
Takahashi et al., Purification and Some Properties of Mannanase from Streptomyces sp, Agric. Biol. Chem, (1984), pp 2189–2195.
Bicho et al., The characterisation of a thermostable endo–β–1,4–mannanase cloned from "*Caldocellum saccharolyticum*", Appt. Microbiol Biotechnology, (1991), pp 337–343.
K. G. Johnson, Exocellular β–mannanases from hemicellulolytic fungi, World Journal of Microbiology and Biotechnology 6, (1990), pp 209–217.
Kusakabe et al., Specificity of β–Mannanase from *Penicillium purpurogenum* for Knojac Glucomannan, agric. Biol. Chem., 52 (2), (1988), pp 519–524.
Araujo et al., Studies on the galactomannan–degrading enzymes produced by *Sporotrichum cellulophilum*, Journal of Industrial Microbiology, 8 (1991), pp 229–236.
Colaco et al., Research/Extraordinary stability of enzymes dried in Trehalose: Simplified molecular biology, vol. 10, (1992), pp 1007–1011.
Lôthi et al., Overproduction of an acetylxylan esterase from the extreme thermophile "*Caldocellum saccharolyticum*" in *escherichia coli*, Applied Microbiology biotechnology, (1990), pp 214–219.
Eero Sjoestroem, Wood Chemistry, Fundamentals and Applications, (1981), pp 49–67.
Seely et al., The Cyclic–2–3–diphosphoglycerate from *Methanobacterium thermoautotrophicum* is the D Enantioner, Current Microbiology, vol. 10, (1984), pp 85–88.
Hensel et al., Thermoadaption of methanogenic bacteria by intracellular ion concentration, FEMS Microbiology Letters 49 (1988), pp 75–79.
Scholz et al., Di–myo–inositol–1–1'–phosphate: a new inositol phosphate isolated from *Pyrococcus woesei*, vol. 306, No. 2,3, (1992), pp 239–242.
Kurr et al., *Methanopyrus Kandleri*, gen. and sp. nove. represents a novel group of hyperthermophilic methanogens, growing at 110° C*, Archives of Microbiology, (1991), pp 239–247.

(List continued on next page.)

*Primary Examiner*—Keith D. Hendricks
*Attorney, Agent, or Firm*—Foley & Lardner

[57] ABSTRACT

A method is provided to increase the efficiency with which monogastric animals utilize low caloric content dietary rations. Addition of a hemicellulase enzyme, such as mannanase, to dietary rations that are not supplemented with concentrated fat, or which contain reduced fat content, increases the efficiency with which monogastric animals utilize the rations.

6 Claims, 2 Drawing Sheets

OTHER PUBLICATIONS

Akino et al., Characterization of Three β–Mannanases of an *Alkalophilic Bacillus* sp., Agric. Biol Chem., 52 (3), (1988), pp 773–779.

Robertson et al., The discovery of new biocatalyst from microbial diversity, vol. 46, No. 1, (1996), pp 3–8.

Araujo et al., Hemicellulases of Bacillus species: preliminary comparative studies on production and properties of mannanases and galactanases (date N.A.).

Lôthi et al., Cloning, Sequences Analysis, and Expression in *Escherichia coli* of a Gene Coding for a β–Mannanase from the Extremely Thermophilic Bacterium "*Caldocellum saccharolyticum*", Applied and Environmental Microbiology, (1991), pp 694–700.

Akion et al., Two Bacillus B–Mannanases Having Different COOH Termini Are Produced in *Escherichia coli* Carrying pMAH5, Applied and Environmental Microbiology, (1989), pp 3178–3183.

Whistler et al., Galactomannan from Soy Bean Hulls, vol. 79, (1957), pp 6055–6057.

Terry Stemler, Ingredient Addition: Extending feed processing past the pellet mill, Feed Management, vol. 45, No. 7, (1994), pp 4, 6, 8, 10, 11.

Lesson et al., "Commercial Poultry Nutrition", University Books, Guelps, Ontario (1991), 10–65.

Mullins et al., Abstracts of Papers, Southern Poultry Science Society, (1995), p 11, 26.

R. H. Rouse, Fat Quality—The Confusing World of Feed Fats, Introduction and History, (1993), pp 55–63.

Dibner et al., Effect of Oxidant Stress on Gastrointestinal Structure and Function, (1995), pp 130–137.

Simons et al., Improvement of phosphorus availability by microbial phytase in broilers and pigs, British Journal of Nutrition (1990), pp 525–540.

Petterson et al., Enzyme supplemental of a poultry diet containing rye and wheat, British Journal of Nutrition, (1989), pp 139–149.

Rotter et al., Effects on different enzyme preparations on the nutritional value of barley in chicken diets, Nutrition Reports International, vol, 39, (1989), pp 107–120.

Petterson et al., Enzyme supplementation of broiler chicken diets based on cereals with endosperm cell walls rich in arabinoxylans or mixed–linked B–glucans, Anim. Prod. (1990), pp 201–207.

Haresign et al., "Supplementary Enzymes to Improve the Utilization of Pig and Poultry Diets", Recent Advances in Animal Nutrition, (1987), pp 71–89.

Adams et al., Enzymes from microorganisms in extreme environments, C&EN Reprint, (1995), pp 32–42.

Rue et al., Application of Hemicell in Feed Industry (China Feed) (1995), pp 1–6.

Abelson et al., "Methods in Enzymology", Methods in Enzymology, vol. 160, (1988), pp 596–609.

Waldroup, Dietary nutrient allowances for poultry, Feedstuffs, vol. 67 (30), pp 69–72, 74, 76. (date N.A.).

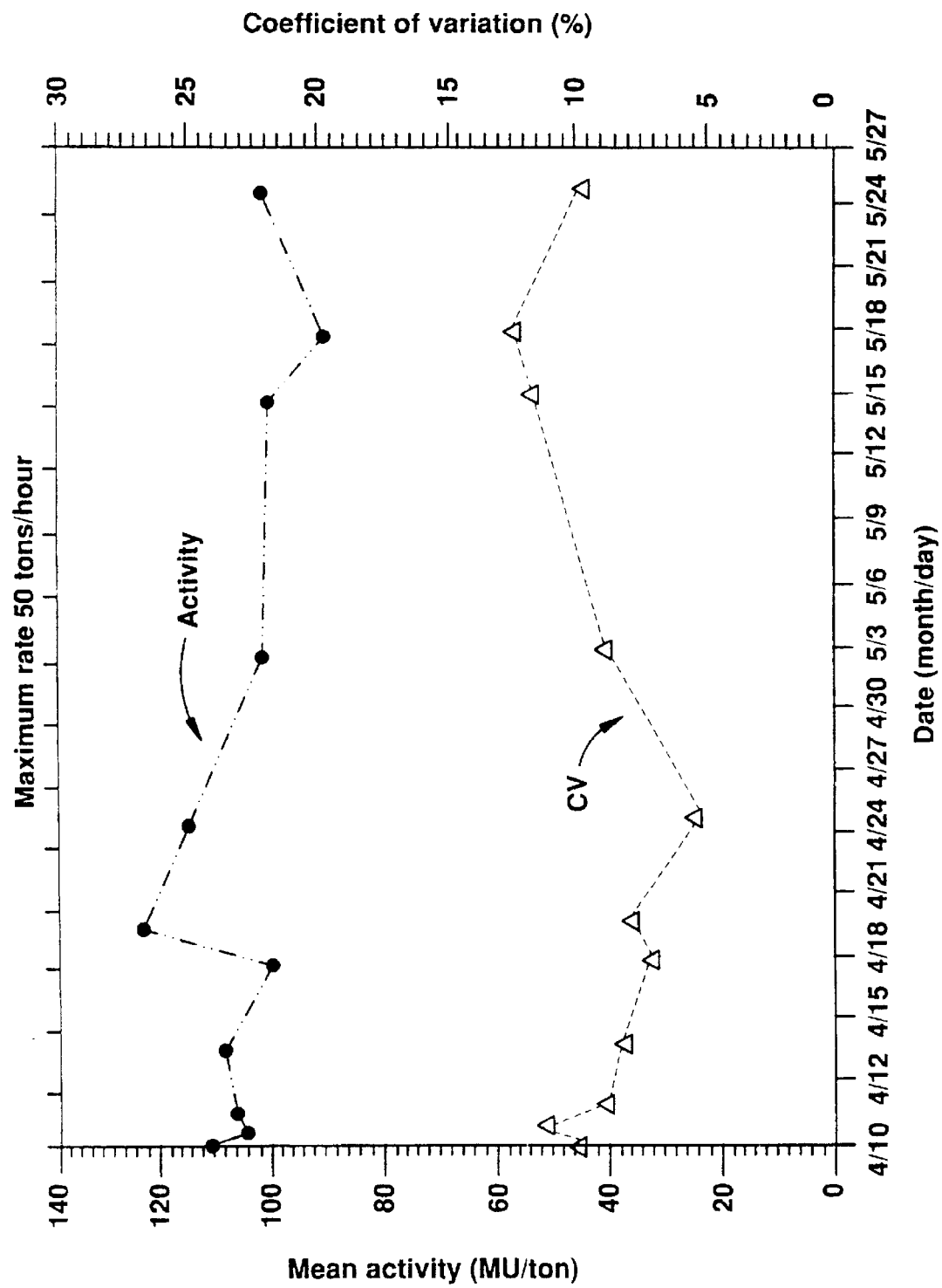

HEMICELLULASE USE IN FEEDS WITH LOW CALORIC CONTENT

This application is based on PCT/US97/05406 filed May 2, 1997, which is based on provisional application 60/038,954 filed May 3, 1996.

BACKGROUND OF THE INVENTION

1. Field of the Invention

The present invention relates to methods for feeding monogastric animals, and more particularly to methods employing one or more hemicellulases, such as mannanase, that decrease the feed to gain, or increase the weight gain of animals fed a low caloric diet containing the enzyme.

2. Background

The world population continues to grow, but land for food production is finite. J. E. Cohen, *Discover* 17: 42–47, (1996). In order to keep up with the growing food demand, improvements in the utilization of food resources will be needed to maintain the current living standards. One approach to improved efficiency has been to enhance the digestion of feeds by the inclusion of enzymes. Chesson, A., Supplementary enzymes to improve the utilization of pig and poultry diets, pp 71–89, In Haresign, W. and D. J. A. Cole (eds), *Recent Advances in Animal Nutrition*—1987, Butterworths, London. Enzymatically aided digestion not only yields more meat per pound of feed, but also reduces the volume of manure and the disposal cost.

Four types of enzymes have been clearly recognized in the marketplace for their value in animal feeds. In diets that contain wheat, rye or triticale, the enzyme xylanase (endo-1,4-β-D-xylanohydrolase, E.C. 3.2.1.8) has been shown to be beneficial. Pettersson et al., *British Journal of Nutrition* 62: 139–149, 1989). Wheat, rye and the wheat/rye hybrid triticale contain large amounts of the non-starch polysaccharide arabinoxylan in the endosperm cell wall. The arabinoxylan is not digested by monogastric animals, but is hydrolyzed by microbial xylanase.

A second example of an enzyme with widespread use in feeds is β-glucanase [cellulase, endo-1,4-β-D-glucan 4-glucanohydrolase E.C. 3.2.1.4; or endo-1,3-(1,3;1,4)-β-D-glucan 3(4)-glucanohydrolase E.C. 3.2.1.6] that has been shown to be especially beneficial in diets containing barley and oats. Rotter et al., *Nutrition Reports International* 39: 107–120 (1989). As well as interfering with digestion, the glucan causes wet sticky manure that induces breast blisters on poultry. In practice, xylanase and β-glucanase are applied together since arabinoxylan and glucan are both present in the cereal grains. Pettersson et al., *Animal Production* 51: 201–20 (1990).

The use of enzymes that cleave phosphorus from phytic acid (myo-inositol hexakisphosphate) is a third example of the beneficial use of enzymes in animal feed. Simons et al., *British Journal of Nutrition* 64: 525–540 (1990). In monogastric animals the phosphate is not released from phytic acid during digestion but is released in the manure through microbial action. Phytic acid has a significant content in typical feeds. Phosphate run-off becomes a problem during manure disposal by causing eutrophication of nearby rivers, lakes or bays. Incorporation of phytase lowers the phosphate content in the manure and significantly decreases the need to add phosphate salts to diets.

Mannanase is another enzyme that has gained commercial use in corn and soybean based diets. The decreased feed to gain, or increased weight gain, of monogastric animals fed a diet containing mannanase was unexpected in a diet based on corn. Until the discovery that bacterial endo-1,4-β-D-mannanase (E.C. 3.2.1.78, also known as mannan endo-1,4-β-mannosidase, see McCleary, B. V., β-D-Mannanase, *Methods in Enzymology* 160: 596–609, 1988) increases feed efficiency in corn-soybean diets, enzymes were infrequently used in poultry or swine feeds grown on corn-soy diets. U.S. Pat. No. 5,429,828, incorporated herein by reference, teaches a method of improving the energy efficiency of hemicellulose-containing animal feed by means of adding a hemicellulase, specifically mannanase, to the diet.

The positive effect of adding endo-1,4-β-D-mannanase on feeding efficiency was unexpected in a diet based on corn. In barley or oats that contain mixed-linked glucan, or wheat, rye and triticale that contain arabinoxylan, the anti-nutritive polymer represents a large percentage of the seed endosperm. In contrast, there is only a very minor content of polymers based on 1-4-β-D-mannan in the common corn based diets. The main source of galactomannan in a typical corn based diet is the soybean meal (added primarily as a source of protein). Based on total sugar analysis and the percentage of non-starch polysaccharides, soybean meal could contain on the order of 1.3% mannan. Thus, a diet with 30% soybean meal would have only about 0.4% mannan polymer. The added energy that would be derived from complete digestion of this small percent of the diet cannot account for the large improvement seen in feed conversion and weight gain.

In many areas of the world, diet rations containing low metabolizable energy content are utilized. Diet rations in these countries are not supplemented with fat. As a consequence, there is a need to increase the energy efficiency for utilization of low fat diets. In developing or developed countries supplemental concentrated fat is being eliminated from the diet for health reasons. In addition, there are a surprising number of problems associated with the addition of concentrated fat to diet rations to increase the metabolizable energy (ME) content of the feed (Rouse, R. H., Fat quality, the confusing world of feed fats, pp 55–63 In: *Proceedings of the 1994 Maryland Nutrition Conference*, March 24–25, Baltimore, Md., University of Maryland Feed Industry Council, College Park, Md.).

Oxidation of unsaturated fatty acids in fat is known to lead to the formation of peroxides and free radicals. This in turn leads to the oxidation of feed nutrients and vitamins. There is also evidence available that indicates that high fat diets can lead to ventricular failure and/or ascites problems in broiler chickens (Mullins, T. M. and W. W. Saylor, Effects of a high fat diet on growth, right ventricular hypertrophy, right ventricular failure, and ascities formation in broiler chickens, Abstract 25, p 11, *Southern Poultry Science Society*, 16th Annual Meeting, Jan. 16–17, 1995, Atlanta, Ga.). Some sources of animal feed fat include restaurant waste fat that has been partially hydrogenated to create un-natural fatty acids with trans double bonds that can interfere with fertility, fatty acid metabolism and the energy value of the feed (Rouse, supra). Another issue is the presence of free fatty acids in commercial fats that can have adverse effects on production and may have an antimicrobial effect in the chicken gut (Rouse, supra). Blended fats are also frequently contaminated with PCBs, pesticide residues, heavy metals, and gossypol from cotton seed oil soapstock (Rouse, supra). Feed mill managers have to be vigilant about all these issues. It is well known that ingested fat (and materials dissolved in it like PCB) can be directly incorporated into the fat of the animal that consumes it and this may present important health risks. In addition, the fat in the animal rations can influence the taste of the meat. For example, more than 1% fish oil in chicken diets will cause a distinct fish-type odor in the meat or eggs (Lesson, S., and J. D. Summers, Chapter 2: Ingredient evaluation and diet formulation, (In) *Commercial Poultry Nutrition*, University Books, Guelph, Ontario, 1991). The effect of high fat content (especially animal fat) on product taste is another issue that some producers are beginning to pay close attention to. The ability to avoid the use of fat and still obtain the same productivity is of general interest.

There is a continuing need for higher efficiency in food production and the urgency of providing solutions will only increase with time. The use of high energy diets which include several percent of fat to promote efficient animal growth is not always possible or desirable due to the high cost of fat or vegetable oils, or limited amounts of available animal fat in some of the most highly populated parts of the world (for example in China and India). There is a basic inefficiency in using the available fat in feed. For example, in the chemical and soap industries the fat could have more value. Finally, there are a number of health issues and problems associated with the incorporation of exogenous concentrated fats in animal diets. These issues are a further indication that a reduced fat, reduced calorie, animal feed diet that maintains high feeding efficiency is urgently needed.

A need therefore exists for a method to increase the efficiency with which monogastric animals utilize feed rations that contain a low metabolizable energy content. Likewise, a need exists for a food ration that can be utilized efficiently by monogastic animals without addition of fat.

SUMMARY OF THE INVENTION

Accordingly, it is an object of the present invention to provide a method to increase the efficiency with which monogastric animals utilize feed rations that contain a low metabolizable energy content.

It is a further object of this invention to provide a method to increase the efficiency with which monogastic animals utilize feed rations which contain no added concentrated fat.

These and other objects are achieved, in accordance with one embodiment of the present invention by the provision of a feed composition comprising (a) a legume seed meal; (b) essential amino acids and (c) and a hemicellulase enzyme, wherein said feed composition has a total metabolizable energy content of less than 3086 Kcal/Kg.

Another embodiment of the invention is a feed composition comprising (a) a soybean meal; (b) essential amino acids and (c) and a hemicellulase enzyme, wherein said feed composition has a total metabolizable energy content of less than 3086 Kcal/Kg.

Another embodiment of the invention is a feed composition comprising (a) a soybean meal; (b) essential amino acids and (c) and a mannanase, such as endo-1,4-β-D-mannanase, wherein said feed composition has a total metabolizable energy content of less than 3086 Kcal/Kg.

Yet another embodiment of the invention is a feed composition comprising (a) a soybean meal; (b) essential amino acids and (c) and a mannanase, such as endo-1,4-β-D-mannanase, wherein said feed composition has a total metabolizable energy content of less than 3086 Kcal/Kg and contains essentially no added concentrated fat.

Another embodiment of the invention is a feed composition comprising (a) a soybean meal; (b) essential amino acids and (c) and a mannanase, such as endo-1,4-β-D-mannanase, wherein said feed composition has a total metabolizable energy content of less than 3086 Kcal/Kg and contains less than 2% added concentrated fat.

BRIEF DESCRIPTION OF THE DRAWING

FIG. 2 shows an example of Successful Enzyme Application at a Feed Mill Producing up to 50 Tons of Pelleted Feed per Hour according to the present invention.

DETAILED DESCRIPTION OF THE PREFERRED EMBODIMENTS

Figure 1:
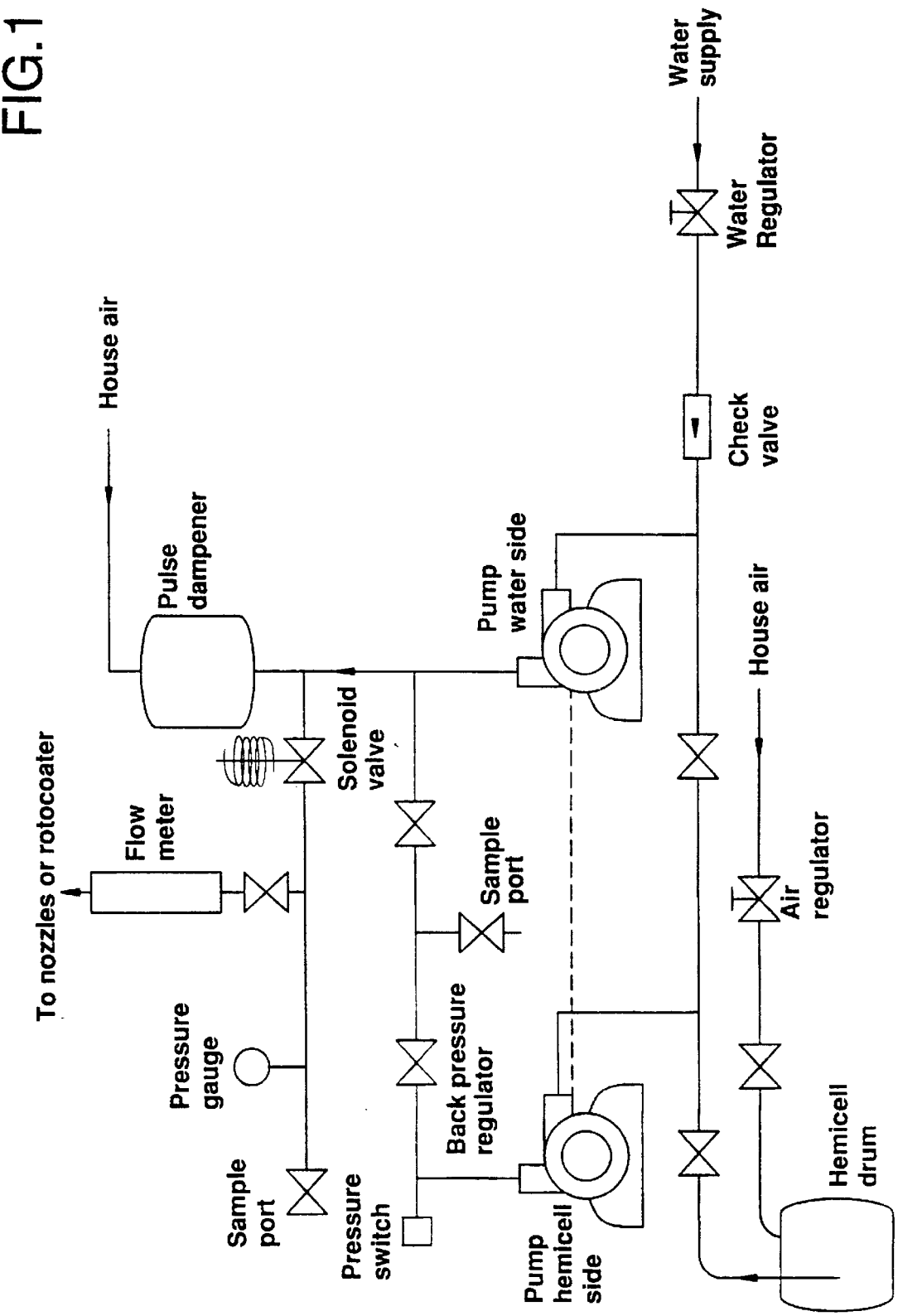
FIG. 1 shows a Pump Flow Diagram—Dual Head—for Feed Mill endo-1,4-β-D-mannanase application according to the present invention.

Any hemicellulase, including any mannanase, and more specifically endo-1,4-β-D-mannanase, that is effective in decreasing feed to gain, or increased weight gain, of an animal that consumes a low fat diet can be utilized in the present invention. As an example, one preferred enzyme source is *Bacillus lentus* (ATCC 5045) endo-1,4-β-D-mannanase (Fodge and Anderson, supra; Fodge, Anderson, and Pettey supra) manufactured as a product with the trade name Hemicell®.

When assessing the value added by the enzyme, a "Point" system is frequently used that is the sum of "weight" points ($P_W$) and "feed conversion, FC" points ($P_{FC}$) The FC is calculated by dividing the weight of feed consumed by the live weight. The two types of points are defined as follows:

$$P_W = (\text{Weight}_{TEST} - \text{Weight}_{CONTROL})/0.06 \text{ lb. (at 45 days)}$$

$$P_{FC} = (FC_{CONTROL} - FC_{TEST})/0.01$$

In most of the scientific tests conducted in the United States, improvements of roughly 5 to 8 points (see Table 2) were observed in chickens, and comparable results were observed with both turkeys and hogs (data not shown). However, occasionally, dramatically better improvement upon endo-1,4-β-D-mannanase application was observed (Rue, J. R., H. R. Zhang, Z. C. Liang, T. Li and F. R. Meng, Application of endo-1,4-β-D-mannanase in Feed Industry, *Zhongguo Siliao* (*China Feed*) 24: 19–21, 1995).

Experiments were conducted in four different locations in China by one of the inventors. Averaging the results from four-tests, there was an improvement of 24.6 points upon endo-1,4-β-D-mannanase use. The data of Rue et al. are summarized in Table 1. The differences between the diets used in the Chinese tests and the typical U.S. diets were examined. Based on the differences, we undertook some carefully controlled scientific trials to investigate the cause of the greater β-mannanase impact. The unexpected result was that fat content, and/or the kilocalorie content of the ration, was key to enhancing the endo-1,4-β-D-mannanase effect as further described below.

TABLE 1

The Effect of endo-1, 4-β-D-mannanase in Chicken Broiler Pen Trials in China (Rue, R. J., et al., 1995)

| Location | Chickens in Trial | Testing Period | Average Weight Increase | Feed to Gain Decrease | Total Points $P_W + P_{FC}$ |
|---|---|---|---|---|---|
| Beijing | 2,000 | 52 days | 0.472 | 0.17 | 24.8 |
| Qungdao, Shangtun | 2,400 | 56 days | 0.419 | 0.30 | 36.9 |

TABLE 1-continued

The Effect of endo-1, 4-β-D-mannanase in Chicken Broiler Pen Trials in China (Rue, R. J., et al., 1995)

| Location | Chickens in Trial | Testing Period | Average Weight Increase | Feed to Gain Decrease | Total Points $P_W + P_{FC}$ |
|---|---|---|---|---|---|
| Province |  |  |  |  |  |
| Lenyun Harabor, Kiangsu Province | 4,700 | 29 days | 0.220 | 0.09 | 12.7 |
| Weifang, Shangtun Province | 4.000 | 49 days | 0.417 | 0.17 | 23.9 |

The mannanase concentration is adjusted to 1000 MU/liter as determined by a reducing sugar assay. The enzyme concentration can also be determined, for example, with a viscosity assay or a blue dye based assay. Generally the blue dye assay is used as a rapid assay to monitor the progress of fermentations, and the reducing sugar assay is used for quality control assays of the final product and feed samples. The final product has a pH adjusted to between 7.0 and 7.5 and the enzyme solution is stabilized against secondary microbial growth by the addition of 150 g/Liter sodium chloride. In this form, the enzyme is very stable and is maintained at ambient temperatures until use.

The enzyme product is preferably applied to feed in two ways. In a first method, the enzyme is dried onto soybean grits (20–80 mesh, Archer Daniels Midland) using a Glatt Air fluidized bed drier at an enzyme concentration of 100 MU per pound. The final moisture content of the dried enzyme product is preferably maintained to less than 8%. This product is added when the feed is formulated and is blended at a rate of one pound of endo-1,4-β-D-mannanase dry product per 2000 pounds of feed. The dry product method is generally used when the mixed feed is not heated to high temperature (e.g. less than 160° F.) during processing for formation into pellets.

A recent trend in feed manufacture is the use of very high temperatures in feed pelleters and/or feed expanders and extruders. Therefore, in many instances the endo-1,4-β-D-mannanase enzyme liquid product may be sprayed onto pre-formed feed pellets at a rate of 100 Mu/ton. At a location in the feed production line downstream from a pellet cooler, falling feed is preferably spread into a wide but shallow depth flow by means of a cone or plate in the pipe or duct just before the area where the enzyme is sprayed on. Thus, about 100 ml of liquid endo1,4-β-D-mannanase per ton of feed is continuously diluted with water using a dual head pump and sprayed through a nozzle at moderate pressure in a uniform pattern onto the falling feed stream. Alternatively, the diluted enzyme is dropped onto a spinning disk which in turn sprays the enzyme onto a curtain of feed passing around the disk by the so-called roto-coater method.

Yet a third method is to spray the enzyme into a pellet mixing device usually located after some other liquid feed component has been applied such as fat or vitamins. The amount of moisture added to the feed in this process is insignificant so that the enzyme is immediately absorbed and the added moisture does not promote microbial growth or erode pellet structure. After enzyme addition, the feed passes through a mixer to make sure uniform distribution of the enzyme in the feed is obtained. Machinery that maintains a uniform flow rate of feed past the spray is preferred.

In a most preferred mode of the spraying process, either a flow meter device as manufactured by Milltronics, Arlington Tx., that provides for adjustment of the spraying rate based on feed flow rate, or a roto-coater device as manufactured by APEC (Automated Process Equipment Corporation), Lake Odessa, Mich. is utilized (Stemler, T., Extending feed processing past the pellet mill, *Feed Management* 45: 4, 1994). The coefficient of variation for enzyme level in the feed should be 15% or less in a preferred case. Application of more than the target amount of 100 MU enzyme per ton of feed is not deleterious, but likely provides little or no added benefit. A more detailed description of a preferred mode of enzyme application and the equipment set up for use at a high temperature feed pelleting mill is given in Example 3 below.

A large number of animal feeding pen trials and full scale field trials have been conducted with endo-1,4-β-D-mannanase as described above. In cases where tests are properly conducted with enough repetitions to yield statistically significant results, and where the enzyme was uniformly applied at the proper level, and other common pitfalls such as non-uniform feeds were avoided, the data generally support increased feed efficiency with incorporation of mannanase into the feed. Six pen trial chicken feeding experiments are summarized in Table 2. Studies were also conducted with turkeys, and hogs of various breeds, with various feed compositions and geographical locations. Occasionally, tests worked much better than expected as in the Rue et al. supra, test in China (Table 1). Examining the differences in these tests that were out of the ordinary led to the current invention.

TABLE 2

β-Mannanase Performance in USA-Type Diets Containing 48%-Protein Soyabean Meal Improvements

| Date | Term | Feed/Gain Weight | Points | Comment |
|---|---|---|---|---|
| Feb. 1990 | 46 days | 0.042 | 0.27 | 8.7 | 7 repetitions/group, S[1] |
| Sept. 1990 | 46 days | 0.042 | 0.13 | 6.4 | 9 repetitions/group, S |
| Dec. 1990 | 46 days | 0.068 | 0.086 | 8.2 | 8 repetitions/group, S |
| Oct. 1991 | 45 days | 0.053 | 0.078 | 6.6 | 7 repetitions/group, S |
| Oct. 1991 | 45 days | 0.064 | 0.142 | 8.7 | 7 repetitions/group, S |
| Sept. 1993 | 39 days | 0.037 | 0.103 | 5.4 | 7 repetitions/group, all males, S |
| Averages |  | 0.049 |  | 0.099 | 7.4 |

[1]S - statistically significant (P > 0.05)

TABLE 3

Comparison of Major components Typical U.S. Broiler Chicken Rations and the Diets Used by Rue et al., in China

| | Typical U.S. Broiler Ration | | |
|---|---|---|---|
| Ingredients | Starter 0–21 days | Grower 22–35 days | Withdrawal 36–43 days |
| Corn | 57.42% | 61.20% | 63.85% |
| SBM 48 | 27.40% | 23.80% | 21.31% |
| Bakery by-product | 2.00% | 5.25% | 6.00% |
| Fat | 3.56% | 3.11% | 2.92% |
| Poultry meal Composition | 6.00% | 3.00% | 3.00% |
| % of NRC lysine | 100% | 100% | 118% |
| Crude protein | 22.5% | 19.0% | 18.5% |
| β-mannan | 0.336% | 0.292% | 0.261% |
| ME (Dcal/Kg) | 3,146 | 3,190 | 3,234 |

TABLE 3-continued

Comparison of Major components Typical U.S. Broiler Chicken Rations and the Diets Used by Rue et al., in China

| | Typical China Broiler Ration | | |
|---|---|---|---|
| Ingredients | 1–14 days diet | 15–45 days diet | 49 day - market diet |
| Corn | 62% | 60% | 73% |
| SBM 44 | 33% | 26% | 22.5% |
| Fish meal | 2% | 2% | 1.5% |
| Composition | | | |
| % of NRC lysine | 110 | 108 | 126 |
| Crude protein | 23% | 21% | 19% |
| β-mannan | 0.6% | 0.475% | 0.411% |
| ME (Kcal/Kg) | 2,950 | 3,000 | 3,050 |

Table 3 compares the composition of a typical highly optimized U.S. chicken broiler diet with the diets used in the Rue, R. J., et al., 1995 study (Table 1). Both diets are corn-soybean based, but there are some differences. Little or no concentrated fat was added to the Chinese diets and the ME (metabolizable energy) averaged about 6.3% higher in the U.S. diets. Another observation is that the Chinese diet used a 44% protein soybean meal (SBM 44) whereas the US diets used 48% soybean meal (SBM 48). The higher protein percent means there is less fiber in the meal derived from the soybean hulls. Because soybean hulls are rich in mannan (Whistler, R. L. and J. Saarnio, Galactomannan from soybean hulls, *J. Am. Chem Soc.* 79: 6055–6057), the calculated percentage for the amount of galactomannan in the two formulations is on average about 66% more for the Chinese diet, although in both cases quite low. The crude protein levels were similar, but the lysine content in the Chinese diets is significantly higher based on the National Research Council (NRC) recommended level. The U.S. diet in Table 3 would have overall about 4.7% excess lysine on a blended basis, but the Chinese diet has about 13.8% excess lysine compared to the NRC recommendation on a blended basis. Using well designed and carefully conducted chicken growth pen trial experiments, the effects of fat (higher energy diets, Diet B) with endo-1,4-β-D-mannanase were assessed keeping the mannan content low and constant. The details of the feeding experiment are described in Example 1, infra.

The diets used in the feeding trial in Example 1 (described in detail in Example 2) are summarized in Table 4. Diet A had about 3% less fat than diet B in each of the three phases of growth (starter, grower and finisher), but diet A would be approximately 85 Kcal/Kg greater than a typical Chinese broiler diet. The amount of crude protein in the two diets was kept the same and the levels of soybean protein added were very close. The amounts of lysine and other essential amino acids, vitamins and minerals were as close to identical as practical. Diet A had more corn added to make up for the deletion of concentrated fat. This is beneficial because corn costs significantly less than fat. Each diet was tested both with and without endo-1,4-β-D-mannanase.

TABLE 4

Basic Composition of Diets in the Controlled Pen Trial of Example 4

| | Starter 0–21 days | Grower 22–35 days | Withdrawal 36–43 days |
|---|---|---|---|
| Diet A | | | |
| Key Ingredients | | | |
| Corn | 62.40% | 68.40% | 71.40% |
| SBM 48 | 31.10% | 25.00% | 21.40% |
| Added Fat | 0.73% | 1.10% | 1.86% |
| Composition | | | |
| % of NRC lysine | 113% | 108% | 124% |
| Lysine crude | 22.00% | 19.50% | 18.00% |
| Protein | 3,008.5 | 3,085.6 | 3,162.7 |
| ME (Dcal/Kg) | | | |
| Diet B | | | |
| Key Ingredients | | | |
| Corn | 58.60% | 64.60% | 67.60% |
| SBM 48 | 31.70% | 25.60% | 22.00% |
| Added fat | 3.86% | 4.19% | 4.99% |
| Composition | | | |
| % of NRC lysine | 109 | 104 | 121 |
| Crude protein | 22.00% | 19.50% | 18.00% |
| ME (Kcal/Kg) | 3,151.7 | 3,228.9 | 3,306.0 | enzyme in 8 pens with 70 birds per pen. The test was ended at 45 days.

The result of the trial is summarized in Table 5. Using both types of feed there was a highly statistically significant (P<0.05) improvement upon the inclusion of the endo-1,4-β-D-mannanase enzyme. However, the improvement seen by inclusion of endo-1,4-β-D-mannanase in diet A was more than a two fold better than the improvement seen in diet B upon enzyme addition. When examining the Kcal required to produce a pound of bird live weight, the Kcal/live pound decreased by 40 in diet B, but decreased by 91 in diet A. Perhaps most important is the comparison between diet B without enzyme and the lower fat diet A with enzyme. The feed conversions and weights were not statistically different comparing those two cases, but the kcal per live pound decreased by 131 in diet A plus β-mannanase. This data demonstrates it is possible to eliminate 3% fat from diets reducing the Kcal content by about 143 Kcal/Kg without the degradation of performance, if an effective endo-1,4-β-D-mannanase is added at 100 MU/ton as defined.

Due to the high cost of concentrated fat as currently used in the industry, the economic benefit of using diet A plus enzyme is very significant. This surprising result was not anticipated. It is believed that the higher mannan content in SBM 44 is a significant difference between the typical U.S. and Chinese diet that caused the mannanase enzyme to have a greater impact in the Chinese diet. These unexpected results show that fat is also of key importance and that endo-1,4-β-D-mannanase is actually improving the energy level of the feed much more than previously recognized. In order to obtain the full benefit of the Kilocalorie increase in ME upon mannanase use, essential amino acid levels should preferably be adjusted upwards accordingly so they do not become limiting.

TABLE 5

Summary of endo-1,4-β-D-mannanase Enzyme
Effect in Diets with Different Energy Levels

| Treatment | Average Weight (lbs) | Feed Conver. F/G[1] | Kcal/ Live lb. | Points[2] $P_W + P_{FC}$ |
|---|---|---|---|---|
| Chicken Broilers on Diet B | | | | |
| endo-1,4-β-D-mannanase | 4.975[a3] | 1.828[a] | 2,680 | |
| Control | 4.870[bc] | 1.855[b] | 2,720 | |
| Improvement | 0.087 | 0.027 | −40 | 4.2 |
| Chicken Broilers on Diet A | | | | |
| endo-1,4-β-D-mannanase | 4.905[ab] | 1847[ab] | 2,588 | |
| Control | 4.765[d] | 1.911[d] | 2,679 | |
| Improvement | 0.140 | 0.064 | −91 | 8.7 |
| Diet A Plus Hemicellulase vs. Diet B without Enzyme | | | | |
| endo-1,4-β-D-mannanase | 4.905[ab] | 1.847[ab] | 2,588 | |
| Control | 4.870[bc] | 1.855[b] | 2,720 | |
| Improvement | 0.035 | 0.008 | −131 | 1.4 |

[1]The F/G is corrected for mortality by including the weight of dead birds in the total weight.
[2]Feeding improvement points as defined in the text above.
[3]Numbers within a column that have different letter superscripts are statistically different (P < 0.05) as determined by ANOV analysis and Least Significant Differences.

The feed enhancement method of this invention is not unique to any one source of endo-1,4-β-D-mannanase. Other mannanases effective in this method can readily be identified after isolation from nature and production through conventional, or recombinant DNA technology well-known in the art. Mannanase coding genes have been isolated from several sources (Luthi, E., N. B. Jasmat, R. A. Grayling, D. R. Love and P. L. Bergquist, Cloning, sequence analysis, and expression in *Escherichia coli* of a gene coding for a β-mannanase from extremely thermophilic bacterium *Caldocellum saccharolyticum, Appl. Environ. Microbiol.* 57: 694–700, 1991; Akino, T., C. Kato, and K. Horikoshi, Two Bacillus β-mannanases having different COOH termini are produced in *Escherichia coli* carrying pMAH5, *Appl. Environ. Microbiol.* 55: 3178–3183, 1989). Further, enzymes can be improved for use in this method by the techniques collectively known as protein engineering, well known in the art. Changes in protein structure are made through changing the DNA coding sequence through mutation. For example, mannanases can be improved in stability through changing specific residues in the amino acid sequence that yield decreased oxidative susceptibility, proteolytic susceptibility, or alternatively, a more ridged structure at increased temperatures. Such changes can be readily predicted after determination of the protein's three-dimensional crystal structure by x-ray crystallography. Alternatively, improvements can be made by area directed, but random mutagenesis of the gene sequence, followed by screening the resulting mutant enzymes for desired improved properties.

In a preferred mode of the invention, a mannanase is utilized that has increased thermal stability that can withstand the steam heat treatment delivered to feed during pelleting, expansion, or extrusion. In this case, the enzyme is preferably directly incorporated in a dry form with the other feed ingredients before pelleting. Increased thermal stability can be accomplished, for example, by a combination of methods. One is to start with enzyme that has inherent thermal stability such as an enzyme isolated from a thermophilic microorganism. However, the specific activity must be sufficient at 40° C. to deliver about 100 MU/ton as described in this method. A second option is to increase the thermostability of a mesophilic enzyme through protein engineering as mentioned above or random mutation area directed mutagenesis and selection for enzymes with improved properties. Yet a third option is to mix the enzyme with stabilizing chemicals and/or add coatings that prevent steam penetration, but which do not interfere with ready solubilization and activity in the animal gut.

Certain sugars like threalose (Colaco, C., S. Sen, M. Thangavelu, S. Pinder and B. Roser, Extraordinary stability of enzymes dried in threhalose:simplified molecular biology, *Bio/Technology* 10: 1007–1011, 1992; Roser, B. J. Protection of proteins and the like, U.S. Pat. No. 4,891,319) are known to stabilize proteins. Also, certain chemicals such as cyclic-2,3-diphosphoglycerate (Seely, R. J. and D. E. Fahrney, The cyclic-2,3-diphosphoglycerate from Methanobacterium thermoautotrophicum is the D-enantiomer, *Current Microbiol.* 10: 85–88, 1984 ; Hensel, R. and H. Koning, Thermoadaptation of methanogenic bacteria by intracellular ion concentration, *FEMS Microbiol. Lett.* 49: 75–79, 1988) and di-myo-inositol-1,1'-phosphate (Scholz, S., J. Sonnenbichler, W. Schafer, and R. Hensel, Di-myo-inositol-1,1'-phosphate: a new inositol phosphate isolated from Pyrococcus woesei, FEBS 306: 239–242, 1992) as well as high salt concentrations (Breitung, J., R. A. Schmitz, K. O. Stetter and R. K . Thauer, $N^5$, $N^{10}$-methylenetetrahydromethanopterin cyclohydrolase from the extreme thermophile *Methanopyrus kandleri*: increase of catalytic efficiency and thermostability in the presence of salts, *Arch. Microbiol.* 156: 517–524, 1991) are known to be involved in the stabilization of proteins in some extremely thermophilic microorganisms. Thus, thermophilic enzymes, stabilizing mutations, stabilizing chemicals or a combination of these factors can be used to prepare mannanases that withstand heating during feed pellet formation in one preferred mode of this invention.

Mannanase-producing microorganisms are readily selected from nature by selecting microbes capable of growing on a mannan based gum as the sole carbon source. Any soil rich in organic matter would be expected to be a good possible source of these microbes. For example, many types of tree wood hemicellulose are known to contain significant amounts of mannan (Sjostrom, E., Chapter 3, Wood Polysaccharides, In *Wood Chemistry, Fundamentals and Applications*, pp49–67, Academic Press, New York, 1981). Thus, sites with decaying wood are likely to be rich sources of mannanases. Certain types of agricultural locations would also be expected to be rich sources of microbes that produce mannanase. For example, sites for the growth and processing of legume seed plants, coffee plants, coconut/copra processing, or the growth and processing of other botanical species that are known to be a rich source of mannan will likely have abundant mannan degrading microbes that produce endo-1,4-β-D-mannanases. Several sources of endo-1,4-β-D-mannanases have already been described (McCleary, B. V., β-D-Mannanase, *Methods in Enzymology* 160: 596–610, 1988;) including fungi (Johnson, K. G., Exocellular β-mannanases from hemicelluloytic fungi, World *J. Microbiol. Biotechnol.* 6: 209–217, 1990; Araujo, A. and O. P. Ward, Studies on the galactomannan-degrading enzymes produced by *Sporotrichum cellulophilum, J. Industrial Microbiol.* 8: 229–236, 1991; Kusakabe, I., G. G. Park, N. Kumita, T. Yasui and K. Murakami, Specificity of β-mannanase from *Penicillium purpurogenum* for Konjac glucomannan, *Agric. Biol. Chem.* 52: 519–524, 1988)

extreme thermophiles (Luthi et a.l., 1991, supra; Bicho, P. A., T. A. Clark, K. Mackie, H. W. Morgan and R. M. Daniel, The characterization of a thermostable endo-β-1,4-mannanase cloned from *Caldocellum saccharolyticum, Appl. Micrbiol. Biotechnol*, 36, 337–343, 1991), hyperthermophiles (Adams, M. W., and R. M. Kelly, Enzymes from Extreme Environments, *Chemical & Engineering News*, pp 32–42, Dec. 18, 1995), Streptomyces (Kusakabe, I., R. Takahashi, β-mannanase of Streptomyces, Methods in Enzymology 160: 611–614, 1988; Takahashi, R., I. Kusakabe, H. Kobayashi, K. Murakami, A. Maekawa and T. Suzuli, Purification and some properties of mannanase from Streptomyces sp. *Agric. Biol. Chem.* 48: 2189–2195, 1984), and Bacillus species (Araujo, A., and O. P. Ward, Hemicellulases of Bacillus species: preliminary comparative studies on production and properties of mannanases and galactanases, *J. Appl. Bacteriol.* 68: 253–261, 1990; Araujo, A. and O. P. Ward, Mannanase components from *Bacillus pumilus, Appl. Environ. Microbiol.* 56: 1954–1956, 1990; Akino et al., 1989, supra; Akino, T., N. Nakamura and K. Horikoshi, Characterization of three β-mannanases of an alkalophilic Bacillus sp., *Agric Biol. Chem.* 52: 773–779, 1988; Emi et al., 1972, supra). Also, mannanases from *Aspergillus niger* are available commercially (two examples are Solvay Enzymes, Hemicellulase and Novo Nordisk, Gamanase™).

Once a microbial population is identified as a potential source of mannanase enzyme based on the ability to grow on mannan as the sole carbon source, individual microbes that secrete mannanase can be readily identified by overlaying cultures grown on Petri dishes with blue dye modified mannan dissolved in molten agarose solutions. After the agarose solidifies, mannanase producing microbes generate apparent clearing zones caused by rapid diffusion of the blue dye labeled mannan fragments. Once identified, standard methods including genetic improvement (Rowlands, R. T., Industrial strain improvement: mutagenesis and random screening procedures, *Enzyme Microb. Technol.* 6: 3–10, 1984) and fermentation technology both well known in the art are used to produce enough enzyme for testing. Once a useful mannanase is identified, then strain improvements, which could include gene cloning and expression, are used to further improve the enzyme production by fermentation methods. In some cases, it may even be advisable to clone the mannanase gene prior to sub-culturing and purifying individual microbial species that produce the mannanase. DNA can be isolated directly from natural sources, cloned into expression vectors in, for example, *E. coli*, followed by screening the recombinant clones for production of the desired mannanase (Robertson, D. E., E. J. Mathur, R. V. Swanson, B. L. Marrs, and J. M. Short, The discovery of new biocatalysts from microbial diversity, *SIM News*, 46:3–8, 1996).

An alternative source of mannanase useful in this application is from a botanical source. Because mannans are frequently used as storage polymers in seeds, certain germinating seeds such as Lucerne (*Medicago sativa*) or Guar (*Cyamopsis tetragonolobus*) are good sources of mannanases (McCleary, 1988, supra). Seeds would be germinated, then processed to yield a concentrated source of enzyme. Alternatively, complete germinating seeds could be ground into a meal for direct use in the feed. In this case, the seeds could have two purposes in the feed, first as a source of mannanase enzyme, but secondly as a source of protein and carbohydrate. However, if germinating seeds have some other anti-nutritive property that overpowers the mannanase effect, then that type of seed would not likely be significantly useful in this method. It is also possible to genetically engineer plants to cause a mannanase to be produced in their fruits, seeds, stems or leaves. As one example of numerous examples that could be cited, foreign enzyme has been expressed in *Brassica napus* (van Rooijen, G. J. H., and M. M. Moloney, Plant seed oil-bodies as carriers for foreign proteins, *Bio/Technology* 13: 72–77, 1995) a commercial oil seed plant that is grown on a large scale. Plant genetic engineering is yet another possible source of mannanase enzyme well known in the art that can be used for the practice of this invention.

Yet another approach to introduce mannanase in feed in the digestive tract, and a preferred mode of this invention, is to genetically modify the animal (i.e hogs, chickens or turkeys) such that endo-1,4-β-D-mannanase is synthesized in the digestive tract. This is accomplished by introducing a mannanase gene with an altered structure such that it is under the control of regulatory sequences that normally regulate the production and/or cause the secretion of another digestive enzyme such as for a protease into the digestive tract. By using regulatory sequences from genes that code for enzymes that are secreted into different parts of the digestive tract, mannanase secretion can be directed to different locations to optimize its impact. This type of transgenic technology has been used, for example, to cause the production of heterologous proteins into milk in the mammary glands of engineered animals (Campbell, A. M., Transgenic technology, *Biopharm* 9: 28, 1996; Velander, W. H., J. L. Johnson, R. L. Page, C. G. Russell, A. Subramanian, T. O. Wilkins, F.C. Gwazdauskas, C. Pittius, W. N. Drohan, High-level expression of a heterologous protein in the milk of transgenic swine using the cDNA encoding human protein C, Proc. Natl. Acad. Sci. 89: 12003–12007, 1992; Hansson, L., M. Elund, A. Elund, T. Johansson, S. L. Marklund, S. Fromm, M. Stromqvist, and J. Tornell, Expression and characterization of biologically active human extracellular superoxide dismutase in milk of transgenic mice, *J. Biol. Chem.* 269: 5358–5363, 1994).

Independent of the method of manufacture or introduction into the digestive tract, the effectiveness of any individual mannanase in this method must be tested in animal feeding trials. Such a test can best be conducted by a protocol similar to that described in detail in Examples 1 and 2. The enzyme amount added into the test should preferably be determined according to the pH and temperatures as used herein, even if these conditions are not optimal for the enzyme to be tested. Then, 100 MU of enzyme is utilized per ton of feed.

For the purposes of this invention, the following definitions are given with respect to certain aspects of the technology used during the development of this invention. Mannan is considered to be any carbohydrate polymer that can be partially or extensively degraded by the enzyme endo-1,4-β-D-mannanase. Thus, the term mannan includes β-1,4-D-mannan based polymers such as galactomannan that has 1,6 linked -galactose branches (or any other branching sugars) on the 1,4-β-D-mannan polymer backbone, or glucomannan that has some 1,4-β-D-glucose residues interspersed in the main polymer chain. Some practical examples of mannans and their sources according to this definition include guar (*Cyamopsis tetragonolobus*) gum, locust bean gum, tagua palm (ivory nut), copra mannan (palm), salep mannan, coffee mannan, carob (*Ceratonia siliqua*) mannan (Whistler, R. L. and C. L. Smart, Polysaccharide chemistry, Academic press, (1953)), sunflower meal, alfalfa meal, (Tookey et al., *J. Agr. Foods Chem.* 10: 131–133, 1962), sunflower meal and palm date meal (Dusterhbft et al., *J. Science Food Agr.* 59: 151–160, 1992). Galactomannans are very widely spread in nature. For example, galactomannans are present in the endosperm of most, but not all, legume seeds (Whistler and Smart, 1953, supra). Therefore, the beneficial effect of adding an effective mannanase is predicted with any feed containing a significant amount of any legume seed meal that is positive for endosperm mannan.

For the purposes of this invention endo-1,4-β-D-mannanase (E.C. 3.2.1.78) is also described by other names such as mannan endo-1,4-β-D-mannosidase or simply endo-mannanase, mannanase or hemicellulase. An effective mannanase for animal feed applications is defined as an enzyme preparation (purified or crude) with the ability to enzymatically reduce the viscosity of locust bean gum or guar gum solutions, and that is effective in increasing the feed conversion in scientifically controlled feeding trials using diets based on corn/legume seed meal (e.g. soybean meal) diets as first described by Fodge and Anderson (Fodge and Anderson, supra, U.S. Pat. No. 5,429,828). Soybean meal is a current commercial product widely used and available primarily as a source of protein in animal feed diets. Soybean meal is enriched for protein through extraction of the soybean oil and most of the hull and is currently the main source of mannan in highly optimized animal feed diets. Soybean meal is generally available in a form that is 44% crude protein, called SBM 44, or 48% crude protein, called SBM 48 for the purposes of this invention. In developing countries, soybean meals with protein contents lower than 44%, are also available.

The positive interaction of the mannanase effect with low diet ME energy for feeding improvement is predicted with diets that contain other sources of mannan, particularly a source of mannan from other members of the legume family such as peas, beans, lentils, alfalfa and others. The legume plant family for the purposes of this invention is the common name used to signify the Leguminosae or Fabaceae family, also commonly known as the pulse family of plants. Many members of this family, like soybeans, are rich in high quality protein and contain mannan in their endosperm (Whistler and Smart, 1953 supra). Many are desirable as feed components and have improved value through the practice of this invention.

For the purposes of this invention, a unit of endo-1,4-β-D-mannanase is may be obtained by the assay methods described herein. An effective dose of mannanase is equivalent to 100,000,000 units (100 MU) per ton of feed. Hemicell® is the registered trademark of an effective mannanase for the purposes of this invention, but any other effective mannanase could be utilized in this invention.

The metabolizable energy (ME) is the amount of energy (measured in kilocalories/kilogram) in feed that can be digested by an animal. The metabolizable energy for a given feed component varies from species to species of animal consuming it. The approximate ME content of common feed ingredients have been published (Dale, N., Ingredient analysis table:1995 Edition, *Feedstuffs* 67: 24–39, 1995). This information is used by animal nutritionists when balanced diets are formulated, and reformulated on a least cost basis, as the price and availability of feed components vary. For the purposes of this invention, the metabolizable energy of a feed is defined by the summation of the metabolizable energy (ME) supplied by each component at levels defined in the *Feedstuffs* Ingredient Analysis Table (Dale, 1995, supra) or updated versions of this reference.

The NRC essential amino acid requirement for the purposes of this invention is as published in the Feedstuffs reference issue for both swine (Easter, R. A., J. Odle, G. R. Hollis and D. H. Baker, Dietary nutrient allowances for swine, *Feedstuffs,* 67: 40–46, 1995) and poultry (Waldroup, P. W., Dietary nutrient allowances for poultry, *Feedstuffs* 67: 69–76, 1995). The requirement is defined in this reference in terms of the amount of amino acid required per unit of metabolizable energy content of the diet.

For the purposes of this invention transgenic manipulation is defined as causing the production of a protein in an animal through the application of recombinant DNA. Recombinant DNA is defined as in vitro manipulation of DNA, whether isolated form natural sources or completely chemically synthesized, followed by introduction into a organism for the purpose of subsequent expression. Mutation is defined as changing the DNA sequence of a gene by either area directed, site directed or random mutagenesis for the purposes of this invention.

Endo-1,4-β-D-mannanase is readily measured by any known method; for example, by a reducing sugar assay.

In an exemplary reducing sugar assay, the following materials are used:

3,5-dinitrosalicyclic acid (DNS), Aldrich, >98% pure

Phenol-reagent grade

Rochelle salt (potassium, sodium tartrate), reagent grade sodium hydroxide (NaOH)

hydrochloric acid (HCl)

sodium sulfite (anhydrous)

locust bean gum (Sigma Chemical Co., product # G0753)

Trishydroxymethylaminomethane (Tris) Buffer

D(+)-mannose, reagent grade (Sigma, product # M-4625)

tetracycline-HCl

40° C. water bath boiling water bath

Sorvall table top centrifuge microcentrifuge (e.g. Eppindorph, 1.5 mL plastic tubes)

vortex mixer spectrophotometer (for reading at 550 nm)

pH meter

16×100 mm glass tubes

13×100 mm glass tubes magnetic stir bars and magnetic stirring/heating plate beakers, volumetric flasks, storage bottles analytical balance variable pipetting device (1 mL) with disposable tips 250 mL baffled shake flasks (Bellco)

Platform flask shaker (New Brunswick Scientific)

Dinitrosalicylic Acid (DNS) Reagent may be used as a reagent. To make 1 liter of a stable stock solution, the following ingredients are dissolved in water.

| | |
|---|---|
| NaOH | 10 g (added first) |
| DNS | 10 g |
| phenol | 2 g |
| Rochelle Salt | 200 g |

The solution is aged 1 day prior to use and stored in the dark. A working solution should be prepared daily by adding 0.5 g/liter anhydrous sodium sulfite to the stock solution.

Locust Bean Gum (LBG) Substrate may be prepared at 5 g/liter by slowly adding LGB into a fast stirring solution of 50 mM Tris Buffer (pH 7.5) at room temperature. After the powder is well dispersed, heat the suspension slowly to boiling and simmer for 1 hour with fast stirring on a heated stir plate to get a very consistent, well hydrated gel. Make sure there are no small clumps of non-hydrated gel in the solution. If there are, start over using slower addition of the LBG to the Tris buffer solution. Cool to room temperature and adjust the solution to the desired final volume to give 5 g/liter LBG. Add tetracycline-HCl (30 mg/mL) to the gum solution as preservative. Store at 4° C when not in use. After storage, mix well prior to use.

Standard Solutions and Standard Curve may be obtained by preparing a series of D-(+)-mannose standard solutions dissolved in water in the concentration range of 0.1 to 0.5 g/liter. Add 0.6 mL of each mannose standard (in duplicate or triplicate) with 1.5 mL of DNS working solution in 13×100 mm glass tubes. Also include a reaction with a 0.6 mL aliquot of water as a reagent blank to zero the spectrophotometer. Heat in a boiling water bath for 5 minutes, cool to ambient temperature and read the absorbance at 550 nm. The expected result is a linear dose response between 0.25 and 1.7 O.D. units. [Note—In enzyme assays (described below), only data generated in the range of 0.25 to 1.2 O.D. is used in calculations because due to substrate limitation, the enzyme reaction is not linear beyond this range]. Calculate the slope of the standard curve (O.D 550/g/liter mannose) from the linear portion of the curve only.

This standard curve will vary with the Lot of DNS reagent obtained. If numerous assays are anticipated, it is advisable to obtain a large lot of DNS when purchased. A typical standard curve is shown in the attached figure. Slope of this curve equals 4.706 O.D/g/liter Mannose.

The samples are prepared by diluting liquid samples to approximately 100,000 U/liter (0.1 MU/liter) in 20 mM Tris-HCl buffer (pH 7.5). For the best accuracy, first determine the density of the enzyme solution, then make use of an analytical balance to very accurately make the dilutions by weight. Solid samples of animal feed are extracted prior to assay. Add 10 grams of solid enzyme carrier to 100 mL of water in a 250 mL non-baffled shake flask and mix at 200 rpm at room temperature for 30 minutes. Transfer some of the extract solution to an Eppindorph centrifuge tube and centrifuge (10,000–12,000 RPM) for 2 minutes. Remove some of the clear liquid supernatant and dilute into 20 mM Tris-HCl buffer (pH 7.5) to about 0.1 MU/liter for assay.

In an enzyme assay, all assays are preferably done in duplicate or triplicate at each dilution level tested. Weigh 4 grams of LBG substrate into 16×100 mm glass tubes and bring to 40° C. in a water bath. [Note—weighing the LGB solution is most accurate because its viscosity makes it difficult to pipette.] Add 0.8 mL of enzyme solution, mix vigorously with a vortex mixer, replace in the 40° C. bath and begin timing. Include a tube with water in place of enzyme as control to zero the spectrophotometer. The enzyme reaction should be mixed about every 5 minutes and immediately before taking samples. At times of 12, 18 and 24 minutes remove a 0.6 mL aliquot of the reaction and add to 1.5 mL DNS working reagent in a 13×100 mm glass tube. Immediately vortex to stop the reaction. Place in a boiling water bath for exactly 5 minutes. Cool to room temperature, centrifuge for 10 minutes at 2,700 RPM in a table top centrifuge and read the supernatant optical density (O.D.) at 550 nm. Using readings that produce numbers in the linear range of the assay (between 0.25 and 1.2 O.D. 550), calculate the enzyme rate as O.D./minute.

A ChemGen unit for Hemicell mannanase has an arbitrary definition that was originally defined from a viscosity method. The size of the unit was chosen based on certain performance characteristics and cannot be directly compared to other assay methods without a conversion factor. When the viscosity method was correlated to the reducing sugar method described here, 1 CG Unit produces 0.574 microgram reducing sugar/minute from LBG. Thus 1 CG MU produces 0.574 gram reducing sugar/minute.

In practical terms, the calculation can be performed in the following way.

$$\frac{O.D./min. \text{ (assay)}}{O.D./g/liter \text{ mannose}} = g/liter/min. \text{ of mannose (Std. curve)}$$

$$\frac{g/Liter/min. \text{ of mannose}}{0.94914 \text{ g/Liter/min.}/MU/Liter} MU/Liter \text{ (in assay soln.)}$$

For endo-1,4-β-D-mannanase-Liquid
  MU/Liter (in assay soln.)×diln. factor=MU/Liter (orig. soln)
For endo-1,4-β-D-mannanase-Dry :
  MU/Liter (in assay soln.)×diln. factor=MU/Liter (orig. extrt.)
  MU/Liter (orig. extrt.)×0.1 Liter/0.01 kg=MU/kg
Endo-1,4-β-D-mannanase may also be obtained by a viscosity assay.

This method is a very sensitive assay for mannanase type activities that hydrolyze the internal manosidic bonds of Locust Bean gum. The corresponding reduction in substrate viscosity is measured with a calibrated viscometer and used to calculate the unit of activity defined by ChemGen (CG Unit). This assay is used where the activity to be measured is low or high accuracy is needed. However, the procedure is time consuming.

The following apparatus and materials are preferably used:
Viscometer. Use a size 100 calibrated Cannon-Fenske type viscometer or its equivalent. A suitable viscometer is supplied as Catalog No. 2885–100 by Scientific Products, 1210 Waukegan Road, McGaw Park, Ill. 60085.
Glass Water Bath. Use a constant temperature glass water bath, maintained at 40° C.±0.1° C. A suitable bath is supplied as Catalog No. W3520-10 by Scientific Products.
Two electronic timers
pH meter
beakers, volumetric flasks (1000 mL, 500 mL)
NaOH, HCl
glycine (reagent grade)
magnetic mixer/hot plate and magnetic stir bars
10 mL pipettes, 2.0 mL pipettes
1.0 mL pipettor with disposable tips (e.g. Pipettman, Rainin Instruments)
0.1 mL pipetor with disposable tips (e.g. Pipetteman, Rainin Instruments)
analytical balance
18×150 mm glass tubes
suction device (designed for use with pipettes)
tube vortex mixer
aluminum foil The following reagents and solutions are preferably used in the viscosity assay:
A. Locust Bean Gum (LBG). Powdered Locust Bean Gum supplied by Sigma Chemical Company may be used. Locust Bean gums will loose viscosity with time. For accurate results, substrate should be prepared fresh at least once a month. For good substrate, the $T_S$ (see below) should be greater than 110 seconds.

LGB is prepared at 2 g/liter (0.2%) by slowly adding LGB into a fast stirring solution of deionized water at room temperature. Add 2 grams of LBG to about 900 mL of deionized water very slowly with rapid mixing on a stir plate. After the powder is well dispersed, heat the suspension slowly to boiling and simmer with continued fast mixing on a heated stir plate for one hour or more to get a very consistent, well hydrated gel. Make sure there are no small clumps of non-hydrated gel in the solution. If there are, start over using slower addition of the LBG to the water solution. Cool to room temperature and adjust the solution to the desired final volume by quantitatively transferring to a 1000 mL volumetric flask, dilute to volume with water, and mix. After storage, mix well prior to use. The pH of the final solution should be close to pH 6.

B. Glycine Buffer, 2 M (pH 9.0). Dissolve 75 grams of glycine in 450 mL deionized water, add 5 N NaOH with continuous mixing until the pH is 9.0±0.05 unit as determined with a pH meter. Quantitatively transfer to a 500 mL volumetric flask and dilute to volume with water. Verify pH 9.0 pH in the final solution.

C. Sample Preparation. Prepare a solution of the sample in deionized water so that 0.5 mL of the final solution will produce a change in relative fluidity ($F_R$) between 0.035 and 0.045 per minute under the conditions specified in the Procedure below. This corresponds to activity in the range of about 1850 to 2400 CG U/liter in the sample. The linearity of the assay is not guaranteed outside this activity range. For liquid samples make dilutions in water using an analytical balance to measure enzyme and the water added for the best accuracy.

For samples extracted from solids, centrifuge or filter to remove solids that could plug the fine bore of the viscometer.

To perform the procedure and calculation, scrupulously clean the viscometer by drawing a large volume of detergent solution (if necessary to remove adhering residue), followed by water, through the instrument and place the previously calibrated viscometer in the glass water bath at 40° C. in an exactly vertical position. These steps are necessary between each measurement.

Determine $T_w$. Pipette 10 mL of deionized water in the viscometer reservoir and allow a few minutes to equilibrate temperature. Draw the water up into the viscometer past the top mark. Allow the solution to flow back starting a timer when the meniscus falls past the top mark and stopping the timer when the meniscus falls past the second mark. Repeat the measurement several times. The average time is defined as the $T_w$ (efflux time for water).

Determine $T_{Ss}$ and Control Rate. Place 10 mL of the LBG substrate in a 18×150 mm glass tube, add 2 mL of 2.0 M glycine buffer (pH 9.0), mix, cap with aluminum foil and place in the 40° C. water for a few minutes to heat. Add 0.5 mL of water, quickly mix with a vortex mixer, and immediately start the first timer. Pipette 10 mL of the solution to the viscometer reservoir, allow a minute to equilibrate, then draw up the solution and determine the efflux time with the second timer, this will be the $T_S$ (recorded in seconds). Each time the $T_S$ is determined, record the elapsed time ($T_R$, reaction time, recorded in digital minutes) on the first timer when the meniscus falls past the top mark. In the ideal case, the $T_S$ will not change indicating no control loss of viscosity. In this case, $T_S$ for calculations should be the average of the determinations. In some cases however, there is a background rate. For background rates, the substrate efflux values are treated as $T_T$ values for calculation with the corresponding $T_R$ values to calculate a background rate as described below. The first efflux time measured after starting is used as $T_S$ in this background rate calculation. Some lots of substrate may become contaminated with small amounts mannanase type activity. If more than 500 U/L are measured or the initial $T_S$ is less than 110 seconds, it is best to prepare a new substrate solution.

Enzyme Rate. Place 10 mL of the LBG substrate in a 18×150 mm glass tube, add 2 mL of 2.0 M glycine buffer (pH 9.0), mix and place in the 40° C. water for a few minutes to heat. Cap the tube with aluminum foil to prevent water evaporation prior to use. Add 0.5 mL of enzyme dilution, quickly mix with a vortex mixer, and immediately start the first timer to determine $T_R$ values. Pipette 10 mL of the solution to the viscometer reservoir, allow a minute to equilibrate, then draw up the solution. When the meniscus passes the top mark, record the $T_R$ on the first timer and begin determining the efflux time with the second timer, this will be the $T_T$. Immediately redraw the solution above the top mark to obtain a $T_T$ at a second $T_R$. Continue repeating the determinations until a period of about 15 minutes have elapsed after the last $T_R$ measurement. At least four time points are recommended.

To perform the required calculation, the data are used to calculate the relative fluidity ($F_R$) and the normalized reaction time ($T_N$) which is $T_R$ plus half the corresponding efflux time. The calculations are done as follows:

$$F_R = (T_S - T_W)/(T_R - T_W),$$

and $$T_N = 0.5(T_T/60 \text{ s/min}) + T_R = (T_T/120) + T_R$$

Plot the relative fluidities ($F_R$) as the ordinate against four reaction times ($T_N$) as the abscissa. A straight line should be obtained. The slope of the line corresponds to the relative fluidity change per minute ($F_R$/min.) and is proportional to the enzyme concentration. Using the slope through a series of points is a better criterion of enzyme activity than using a single relative fluidity value. Ideally, the relative fluidity change should be about 0.04/minute. If there is background substrate degradation in the reaction, the plot will not be linear in the initial part of the plot. Use the data after the line becomes linear to determine the slope. We generally use the Lotus spreadsheet program to plot and calculate the best fit of the plot slope and to perform the other calculations necessary obtain units.

The CG Units/liter in the 0.5 mL sample added to the reaction are defined as:

$$\text{CG U/Liter} = 9.397 \times 10^4 \times F_R/\text{min.}$$

Thus, the original sample enzyme concentration is calculated as:

$$\text{CG U/L (orig. sample)} = (1 \text{ CG U/L} - \text{Substrate Control U/L}) \times \text{dilution factor}$$

Endo1,4-β-D-mannanase may also be assayed using a blue dye assay.

According to this assay an enzyme substrate is prepared preferably using a procedure (*Methods in Enzymology* 160: 538, 1988) described for the production of RBB(remizol brilliant blue)-xylan that was adapted for attaching the RBB blue dye to locust bean gum. The procedure was modified by adding 0.7% Locust bean gum (LBG) and 0.07% dye into the initial reaction. Also, after the reaction with RBB in sodium acetate and sodium hydroxide, the dyed locust bean gum solution was dialyzed to remove salt prior to ethanol precipitation. This facilitated resuspension of the gum after precipitation. The dye bound gum can be precipitated with one volume of ethanol at room temperature rather than two volumes on ice as used in the xylan procedure.

Dissolve 3.5 g of RBB-LBG in one liter of 50 mM Tris-HCl, pH 7.5 by adding dry powder slowly to a rapidly-stirred buffer. Heat with stirring to boiling, then autoclave for 20 minutes at 121° C. and cool to room temperature. Centrifuge to remove undissolved material. Pour the supernatant into suitable tubes, then autoclave again. The solution is stable for at least six months if no microbial contamination is introduced into the bottles. The reagent blank in the assay (see below) should give an optical density (OD) of less than 0.15 when read against 70% ethanol. If the OD is higher, the RBB-LBG reagent is discarded.

Assay Protocol

A. Make appropriate dilutions of samples and standards in non-chlorinated water. For the standard curve, dilution are made that have about 1.5, 2.0 and 2.5 MU/Liter using an enzyme standard previously determined by the reducing sugar method. The test samples should be diluted so that the activity falls between the 1.5 to 2.5 MU/Liter range. For best results dilutions are made using volumetric flasks and an analytical balance to exactly determine the amount of enzyme solution added.

B. Dispense 0.54 mL of RBB-LBG reagent into 1.5 mL microcetrifuge tubes and place the tubes in a 400 water bath for at least 10 minutes.

C. To start the reaction, add 20 µL of enzyme and mix by vortexing. Incubate each sample for exactly 10 minutes. Samples should be tested in duplicate for best results.

D. Stop the reaction by adding 0.9 mL of absolute ethanol (reagent alcohol) and mixing thoroughly. Allow the tubes to sit at room temperature for at least 10 minutes.

E. Centrifuge the tubes at 8–12,000 RPM in a centrifuge for three minutes.

F. Read the optical density at 590 nm using a reagent blank treated exactly as the test samples above using 20 µL of water instead of enzyme to zero the spectrophotometer.

G. Plot the OD 590 nm observed for the standards against the activity in MU/Liter in the diluted standards and determine the slope.

Calculation

The activity in the samples (MU/Liter)=OD 590 nm×slope×sample dilution factor

The present invention is further described below by reference to the following illustrative examples.

EXAMPLE 1

Chicken Growth Pen Trial Method

Commercial broiler chickens (50/50 male/female Peterson×Arbor Acres) supplied by the ConAgra Hatchery, Hurlock, Md. were grown with 70 birds per pen from day 1 to day 45 and were delivered to the test site on the day of hatching. All chicks were vaccinated and treated as normal at the hatchery. The density was 0.850 ft$^2$ per bird using pens 5 feet by 12 feet in size. The building was a wood/cinderblock structure heated with forced air heating (plus heat lamps the first week) and incandescent lighting. The temperature was monitored daily and maintained at 92° F. for the first 3 days, then reduced 1° F. per day until 70° F. was reached and maintained until the end of the trial. Air exchange was enhanced by fans on time delay that ran on average between 1–4 minutes every 10 minutes. The test was conducted from Oct. 31, 1995 to Dec. 15, 1996 on the Maryland Eastern shore.

Feeds were prepared using known requirements typical to the poultry industry and commercial specifications. The feed for the entire test was all mixed and pelleted at about 175° F. The feed utilized in the experiment was all prepared at the same time and equaled or exceeded the nutritional requirements set by the National Research Council (*Nutrient Requirements of Poultry*, 9$^{th}$ Revised Edition, U.S. National Research Council, 1994). A portion of the control mix was taken for enzyme addition by uniformly spraying it with liquid concentrate. The starter feed for days 0 to 21 was crumbled pellets. Grower and finisher feeds were used as whole pellets.

Twenty five chicks are initially caught and weighed. The mean weight was determined and a range of five grams around the mean was established. Chicks with weights within this range were randomly chosen and divided at 70 per pen. A total of 3,840 female and male chicks (50/50) were used in the experiment. All pens were monitored three times per day during the study. More specifically, the availability of food and water, temperature maintenance, and the general condition of chicks and litter were monitored. For the first seven days of the experiment, chicks that died were replaced with chicks from a pool of birds separately maintained on their respective diets and chosen at random.

The eight pens for each of the different treatments were randomized throughout the building to eliminate any possible bias caused by the physical location of pens in the building. The following data was collected during the trial:

1. Individual body weights on day 21 and day 45. ed efficiency on day 21 and 45.

2. The feeding efficiency was calculated as the feed/gain ratio. The gain was the sum of the live bird weights as well as the weight of any dead birds on the day that they died. The feed weight was determined by adding known amounts of feed to each pen, and subtracting the weight of any uneaten feed left in the pen at the time of weighing the birds.

3. Mortality analysis included the total mortality as well as the day of death.

4. Standard deviations and coefficients of variation were calculated for the individual body weights on day 21 and 45.

5. Other observations of the birds included feathering and physical appearance.

TABLE 6

Pen Trial Body Weight Data, Day 1–45 Average Pen Body Weight (pounds)

| Rep | T1 | T2 | T3 | T4 |
|---|---|---|---|---|
| R1 | 4.819 | 5.026 | 4.822 | 5.080 |
| R2 | 4.850 | 4.946 | 4.831 | 4.936 |
| R3 | 4.974 | 4.881 | 4.657 | 4.819 |
| R4 | 4.885 | 5.021 | 4.793 | 4.841 |
| R5 | 4.892 | 4.918 | 4.705 | 4.809 |
| R6 | 4.946 | 4.943 | 4.695 | 4.849 |
| R7 | 4.782 | 4.895 | 4.794 | 4.955 |
| R8 | 4.812 | 5.025 | 4.823 | 4.950 |
| Mean | 4.870 | 4.957 | 4.765 | 4.905 |
| Stat. | bc | a | d | ab |
| S.D. | 0.063 | 0.056 | 0.064 | 0.087 |
| C.V. | 1.286 | 1.127 | 1.341 | 1.765 |

There were no significant differences observed between any of the groups with respect to mortality, feathering or physical appearance. The results are summarized in Table 5 above and the details of the diet preparations are shown in Example 2 (Table 8). Details of the data are given in Tables 6 and 7.

TABLE 7

Pen Trial Feed Conversion Data, Feed/Gain
1–45 Days Corrected for Mortality

| Rep | T1 | T2 | T3 | T4 |
|---|---|---|---|---|
| R1 | 1.872 | 1.810 | 1.920 | 1.850 |
| R2 | 1.851 | 1.871 | 1.923 | 1.871 |
| R3 | 1.866 | 1.864 | 1.926 | 1.892 |
| R4 | 1.877 | 1.848 | 1.944 | 1.879 |
| R5 | 1.852 | 1.800 | 1.905 | 1.820 |
| R6 | 1.822 | 1.803 | 1.881 | 1.842 |
| R7 | 1.818 | 1.818 | 1.889 | 1.807 |
| R8 | 1.883 | 1.807 | 1.900 | 1.815 |
| Mean | 1.855 | 1.828 | 1.911 | 1.847 |
| Stat. | b | a | d | ab |
| S.D. | 0.023 | 0.027 | 0.020 | 0.030 |
| C.V. | 1.234 | 1.483 | 1.030 | 1.607 |

In Tables 6 and 7, the treatment groups are assigned as follows:

T1=3229 Kcal/Kg, no enzyme

T2=3229 Kcal/Kg, plus enzyme

T3=3085 Kcal/Kg, no enzyme

T4=3085 Kcal/Kg, plus enzyme

EXAMPLE 2

Details of Diets Used in Pen Trials to Assess the Interaction of Diet Energy and Mannanase Table 8 provides a detailed description of the diets used in the pen trial described in Example 4. The ingredients are well recognized by anyone skilled in the art of animal nutrition. The starter diet was used on days 0–21, the grower diet on days 22–39 and the finisher diet on days 40–45.

TABLE 8

Detailed description of diets used in the Pen Trial to Assess Energy Level Effects

| | Weight % - Diet A | | | Weight % - Diet B | | |
|---|---|---|---|---|---|---|
| Component | Starter | Grower | Finisher | Starter | Grower | Finisher |
| yellow corn | 62.381 | 68.415 | 71.406 | 58.593 | 64.627 | 67.618 |
| soybean meal 48% | 31.077 | 24.982 | 21.352 | 31.726 | 25.63 | 22.000 |
| Fat 3700 | 0.731 | 1.063 | 1.857 | 3.858 | 4.191 | 4.985 |
| Salt (NaCl) | 0.307 | 0.305 | 0.258 | 0.307 | 0.305 | 0.258 |
| limestone | 0.537 | 0.583 | 0.544 | 0.527 | 0.573 | 0.533 |
| DEFPHOS 32-18 | 1.258 | 1.095 | 1.077 | 1.267 | 1.104 | 1.086 |
| choline CH-60% | 0.073 | 0.049 | 0.010 | 0.081 | 0.057 | 0.017 |
| meat blend - 58% | 3.000 | 3.000 | 3.000 | 3.000 | 3.000 | 3.000 |
| vitamin premix | 0.025 | 0.025 | 0.025 | 0.025 | 0.025 | 0.025 |
| trace mineral PRX | 0.075 | 0.075 | 0.075 | 0.075 | 0.075 | 0.075 |
| DL-methionine | 0.285 | 0.156 | 0.145 | 0.290 | 0.161 | 0.151 |
| SACOX | 0.100 | 0.100 | 0.100 | 0.100 | 0.100 | 0.100 |
| bacitracin MD | 0.042 | 0.042 | 0.042 | 0.042 | 0.042 | 0.042 |
| cromophyl-Oro Composition | 0.110 | 0.110 | 0.110 | 0.110 | 0.110 | 0.110 |
| lysine (total) | 1.212 | 1.031 | 0.922 | 1.223 | 1.043 | 0.934 |
| methionine + cysteine | 1.020 | 0.83 | 0.788 | 1.020 | 0.830 | 0.780 |
| crude protein | 22% | 19.5% | 18% | 22% | 19.5% | 18% |
| Kcal/Kg | 3008.5 | 3085.6 | 3162.7 | 3151.7 | 3228.9 | 3306.0 |

EXAMPLE 3

Spraying System for Application of Enzyme to Food Pellets at a Poultry Feed Mill In many cases it may be preferable to spray enzyme onto preformed feed pellets if extreme temperatures are used during the formation of the pellets. In some locations heating time and temperatures are used during pellet formation that essentially cook the feed and thus denature most enzymes effective in this method.

FIG. 1 shows a flow diagram of a pumping system for coating feed with enzyme. The pump is a two headed diaphragm pump (Duriron #E2-(16)(07)115-68A31) that is used to pump water and endo-1,4⁻β-D-mannanase in approximately a 9 to 1 ratio into a common outlet. The mixture flows past a pulse dampener (Blacoh #A301N) and a solenoid valve (Asco #EF8210G87) is used to prevent water flow while the pump is off. A flow meter (King Instruments 7511 series) allows visual inspection of liquid flow rates and the color of the water diluted enzyme solution.

The adjustable pressure switch (Omega #PSW121) is used to detect any line blockages and automatically turns off if the pressure setting is exceeded. The setting used depends on the height of the enzyme outlet relative to the pump and is generally slightly greater than the pressure created by the head height. Valves are provided to allow liquid sampling and priming of the endo-1,4⁻β-D-mannanase side of the pump head. House water pressure is reduced to 15 psi before the pump by the water pressure regulator. The endo-1,4⁻β-D-mannanase storage tank or drum may be pressurized to 2 psig with the air regulator to prevent loss of pump prime.

The mixture in the storage tank is provided at 1000 MU/liter and 100 MU is applied to each ton of feed. The water flow rate is adjusted to 900 mL per ton of feed using the stroke length adjuster. The endo-1,4⁻β-D-mannanase flow rate on the other side of the pump is then independently adjusted to 100 mL/ton. The rate is verified by measuring the rate of enzyme concentrate leaving the storage drum or tank. Thus, after water dilution, about 1 liter of diluted liquid enzyme is applied to each ton of feed adding only about 0.1% moisture. In a preferred mode, enzyme is applied to feed through existing mill fat coating equipment known as a roto-coater manufactured by APEC (Automated Process Equipment Co., Laurel Drive, Lake Odessa, Mich., 48849) Typically, enzyme will be piped to the same location where the fat falls onto a spinning dish that disperses it onto a thin curtain of feed falling around the dish at a uniform rate. The fat coating equipment is often at the top of the mill. The elevation change creates enough pressure in the diluted enzyme containing pipe to properly seat the pump check valves for normal operation.

The signal from the mill's computer is run through the normally closed side of the pressure switch to the motor starter, pilot light and solenoid valve. Therefore, when the mill begins making feed, the pumping system is automatically turned on unless there is an over-pressure situation.

Samples of feed are taken where it is loaded into bins or trucks for enzyme level verification. The assay method used is known in the art as described, supra. Success in application is achieved when the mean enzyme level is 100 MU/ton and the coefficient of variation (CV) is less than 15%. FIG. 2 shows an example of successful enzyme application over a period of several weeks at a feed mill capable of producing up to 50 tons of pelleted feed per hour.

What is claimed is:

1. A feed composition comprising (a) a legume seed meal; (b) essential amino acids and (c) a hemicellulase enzyme, wherein said feed composition has an amount of added concentrated fat of less than 2% by weight of the feed composition, and a total metabolizable energy content of less than 3086 Kcal/Kg.

2. A feed composition according to claim 1, wherein the legume seed meal is soybean meal.

3. A feed composition according to claim 1, wherein said hemicellulase is a mannanase.

4. A feed composition according to claim 3, wherein said mannanase is the endo-1,4-$\beta$-D-mannanase produced by *Bacillus lentus* designated ATCC 55045.

5. A feed composition according to claim 1, wherein said feed composition comprises no concentrated fat.

6. A feed composition according to claim 1, wherein the added concentrated fat content is less than 1% by weight of the feed composition.

* * * * *